US006204256B1

(12) United States Patent
Shalaby et al.

(10) Patent No.: US 6,204,256 B1
(45) Date of Patent: Mar. 20, 2001

(54) ACYLATED CYCLODEXTRIN DERIVATIVES

(75) Inventors: Shalaby W. Shalaby, Anderson; Joel Thomas Corbett, Clemson, both of SC (US)

(73) Assignee: Polymed, Fendleton, SC (US)

( * ) Notice: Subject to any disclaimer, the term of this patent is extended or adjusted under 35 U.S.C. 154(b) by 0 days.

(21) Appl. No.: 09/288,471

(22) Filed: Apr. 8, 1999

Related U.S. Application Data

(62) Division of application No. 08/740,778, filed on Nov. 1, 1996, now Pat. No. 5,916,883.

(51) Int. Cl.$^7$ .................................................. A01N 43/04
(52) U.S. Cl. ........................... 514/58; 514/778; 514/784; 514/785; 525/54.2; 530/300; 530/307; 530/311; 530/813; 530/815; 530/817; 536/46; 536/48; 536/103; 536/119
(58) Field of Search ............................. 514/58, 778, 784, 514/785; 530/300, 307, 311, 813, 815, 817; 536/103, 119, 46, 48; 525/54.2

(56) References Cited

U.S. PATENT DOCUMENTS

| | | |
|---|---|---|
| 3,426,011 | 2/1969 | Parmerter et al. . |
| 3,453,260 | 7/1969 | Parmerter et al. .................... 260/209 |
| 4,659,696 | 4/1987 | Hirai et al. ............................... 514/15 |
| 4,670,419 | 6/1987 | Uda et al. ................................ 514/16 |
| 4,727,064 | 2/1988 | Pitha . |
| 4,764,604 | 8/1988 | Muller . |
| 4,869,904 | 9/1989 | Uekama et al. . |
| 5,183,809 * | 2/1993 | Weisz et al. ............................ 514/58 |
| 5,208,316 | 5/1993 | Yoshinaga . |
| 5,241,059 | 8/1993 | Yoshinaga . |
| 5,247,013 | 9/1993 | Shinoda et al. . |
| 5,633,368 * | 5/1997 | Hirsenkorn ........................... 536/103 |
| 5,646,131 * | 7/1997 | Badwan et al. ......................... 514/58 |
| 5,658,894 * | 8/1997 | Weisz ..................................... 514/58 |

FOREIGN PATENT DOCUMENTS

| | | |
|---|---|---|
| 0 437 478 B1 | 7/1991 | (EP) . |
| 2145422 | 3/1985 | (GB) . |
| 06100464 * | 4/1994 | (JP) . |
| 93/03784 * | 4/1990 | (WO) . |
| 9620222 | 7/1996 | (WO) . |

OTHER PUBLICATIONS

Croft, A. P., and Bartsch, R.A., Synthesis of Chemically Modified Cyclodextrins, Tetrahedron, vol. 39, No. 9, pp. 1417–1474, (1983).

Hirayama et al. "Characterization of Peracylated β–Cyclodextrins with Different Chain Lengths as a Novel Sustained Release Carrier for Water–Soluble Drugs", Chem. Pharm Bull. 43:130–136, (1995).

Hirayama et al. "Utilization of Diethyl–β–cyclodextrin as a Sustained–Release Carrier for Isosorbide Dinitrate", J. of Pharmaceutical Sciences 77:233–236, (1988).

Horiuchi et al. "Slow–Release Characteristics of Diltiazem from Ethylated β–Cyclodextrin Complexes", J. of Pharmaceutical Sciences 79:128–132, (1990).

K. Uekama et al., "Sustained Release of Buserelin Acetate, a Luteninizing Hormone–Releasing Hormone Agonist, From An Injectable Oily Preparation Utilizing Ethylated Beta–cyclodextrin", J. Pharm. Pharmacol., 1989, 41:874–876.

Fang–y Liu et al., "Complexation of 6–Acyl–O–Beta–Cyclodextrin Derivatives with Steroids—Effects of Chain Length and Substitution Degree", Drug Development and Industrial Pharmacy, 18(15), 1599–1612 (1992).

H. Ryoshi et al., "Two–phase(Water/Organix) Free Radical Polymerization of Water–Soluble Vinyl Monomers Using Lipophilic Acylated Beta–cyclodextrins As Initiator Carrier", Makromol. Chem. 187, 263–271, 1986.

I. Sugiura et al., "Immobilized Beta–Cyclodextrins Preparation with Various Crosslinking Reagents and the Guest Binding Properties", Bull. Chem. Soc. Jpn., 62, 1643–1651 (1989).

M. Tanaka et al., "Unmodified and Acylated Cyclodextrin Stationary Phases for Liquid Chromatographic Separation of Aromatic Compounds", Journal of Chromatography, 301 (1984) 345–353.

J. J. Torres–Labandeira et al., "Use of Cyclodexrins in Sustained–Release Nifedipine Formulations", Minutes Int. Symp. Cyclodextrins, 6th ED., Hedges, Allan R, Ed., (Ed. Sante, Paris, FR), 1992, pp. 563–566.

K. Uekama et al., Design and In Vitro Evaluation of Slow–Release Dosage Form of Piretanide: Utility of Beta–Cyclodextrin: Cellulose Derivative Compbination as a Modified–Release Drug Carrier, Journal of Pharmaceutical Sciences vol. 79, No. 3, pp 244–248, Mar. 1990.

K. Uekama et al., "Peracylated Beta–Cyclodextrins as Novel Sustained–Release Carriers for a Water–Soluble Drug, Molsidomine", J. Pharm. Pharmacol. 1994, 46: 714–717.

K. Uekama et al., "Ethylated Beta–Cyclodextrins as Hydrophobic Drug Carriers: Sustained Release of Diltiazem in the Rat", Journal of Pharmaceutical Sciences, vol. 76, No. 8, pp 660–661, Aug. 1987.

R. Breslow et al., "Additional Flexibility Solves the Leaving Group Problem in Cyclodextrin Acylation", Tetrahedron Letters, vol. 31, No. 5, pp 631–634, 1990.

H.–J. Thiem et al., "Molecular Modeling Calculations on the Acylation of Beta–Cyclodextrin by Ferrocenylacrylate Esters", J. Am. Chem. Soc. 1988, 110, 8612–8616.

(List continued on next page.)

*Primary Examiner*—Gary Geist
*Assistant Examiner*—Everett White
(74) *Attorney, Agent, or Firm*—John D. Conway; Brian R. Morrill; Fish & Richardsom

(57) ABSTRACT

A cyclodextrin derivative, wherein at least 60 percent of the free hydroxy groups of said cyclodextrin are acylated with acyl groups where at least one of said acyl groups comprise a free carboxylic group.

14 Claims, No Drawings

OTHER PUBLICATIONS

G. L. Trainor et al., "High Acylation Rates and Enantioselectivity with Cyclodextrin Complexes of Rigid Substrates", J. Am. Chem. Soc. 1981, 103, 154–158.

R. Breslow et al., "Improved Acylation Rates within Cyclodextrin Complexes from Flexible Capping of the Cyclodextrin and from Adjustment of the Substrate Geometry", J. Am. Chem. Soc. 102:2, 1980, pp. 762–770.

F. Hirayama, "Development and Pharmaceutical Evaluation of Hydrophobic Cyclodextrin Derivatives as Modified–Release Drug Carriers", Yakugaka Zasshi 113 (6), pp. 425–537, 1993.

J. H. Coates et al., "complementary Diasteroselectivity in the Synthesis and Hydrolysis of Acylated Cyclodextrins", Chemistry Letters, pp. 1153–1156, 1994.

K. Matsubara et al., "Possible Use of Triacetylated Cyclodextrins in the Preparation of Sustained–Release Oily Injection of LHRH Agonist, Buserelin Acetate", Minutes of Int. Symp. Cyclodextrins, 6th ED., Hedges, Allan R, Ed., (Ed. Sante, Paris, FR), (1992), pp. 547–550.

M. F. Czarniecki, et al., "Very Fast Acylation of Beta–Cyclodextrin by Bound p–Nitrophenyl Ferrocinnamate", J. of Am. Chem. Soc., 100:24, 1978, pp. 7771–7772.

Zhong–Yao Shen et al., "Synthesis and Characterization of Cyclomaltheptaose (Z)–2–Butenedioic Monoesters", Carbohydrate Research, vol. 201, No. 2, Jul. 1, 1990, Amsterdam, pp. 241–248.

* cited by examiner

ACYLATED CYCLODEXTRIN DERIVATIVES

CROSS-REFERENCE TO RELATED APPLICATIONS

This application is a divisional application of U.S. patent application Ser. No. 08/740,778, filed Nov. 1, 1996, now U.S. Pat. No. 5,916,883.

BACKGROUND OF THE INVENTION

In 1904, Schardinger first characterized cyclodextrins as cyclic oligosaccharides. The α, β, and γ-cyclodextrins, which consist of six, seven, and eight glucose units, respectively, are the most common natural cyclodextrins.

Cyclodextrins have been used as inclusion complexes by complexing with a guest compound or molecule as a host compound or molecule. Such inclusion complexes have been used to mask the bitter taste or unpleasant odor of a guest compound, to solubilize a hardly soluble guest compound, to enlarge the stability of a guest compound against heat, light, or air, to stabilize emulsions, or as a sustained release preparation using a hydrophobic alkylated cyclodextrin. See U.S. Pat. No. 4,869,904. However, no one has attempted to make carboxyacylated cyclodextrins, or used such cyclodextrin derivatives to form ionic sustained release compositions.

SUMMARY OF THE INVENTION

In one aspect, the present invention features a cyclodextrin derivative, wherein at least 60 (e.g., between 75 and 100) percent of the free hydroxy groups of the cyclodextrin are acylated with acyl groups where at least one of the acyl groups comprises a free carboxylic group. What is meant by cyclodextrin is a cyclic oligosaccharide. Examples of cyclodextrins include α-cyclodextrin, β-cyclodextrin, or γ-cyclodextrin.

In one embodiment the acyl groups are selected from $COE_1$, where $E_1$ is selected from the group consisting of $C_{2-32}$ carboxy alkyl, $C_{3-33}$ carboxy alkenyl, $C_{7-37}$ carboxyaryl, $C_{8-38}$ carboxyaryl alkyl, and $C_{9-39}$ carboxyaryl alkenyl, and $COE_2$, where $E_2$ is selected from the group consisting of $C_{1-30}$ alkyl, $C_{2-30}$ alkenyl, $C_{6-36}$ aryl, $C_{7-37}$ arylalkyl, and $C_{8-38}$ arylalkenyl, wherein at least one of the acyl group is $COE_1$.

In a further embodiment, between 10 and 80 (e.g., between 30 and 80) percent of the free hydroxy groups of the cyclodextrin are acylated with $COE_1$ and between 10 and 80 (e.g., between 15 and 60) percent of the cyclodextrin are acylated with $COE_2$. In still a further embodiment, $E_1$ is $C_{2-10}$ carboxy alkyl (e.g., $COE_1$ is $CO(CH_2)_n COOH$ (where n=2–3)) and $E_2$ is $C_{1-10}$ alkyl (e.g., $COE_2$ is $CO(CH_2)_n CH_3$ (where n=0–5)).

In another aspect, the invention features a copolymer comprising the cyclodextrin derivative described above, wherein the cyclodextrin derivative comprises at least one free hydroxy group which is acylated with a polyester comprising hydroxy acid monomers. In one embodiment, the copolymer has an average molecular weight of between 500–40,000 daltons (e.g., 500–10,000). In a further embodiment, the polyester comprises hydroxy acid monomers selected from the group consisting of lactic acid, glycolic acid, hydroxy caprolic acid, or any optically active isomer thereof. Such polyesters can be manufactured by reacting said cyclodextrin derivative with lactide, glycolide, caprolactone, p-dioxanone, trimethyl carbonate, or any optically active isomer thereof.

In still another aspect, the invention features a composition comprising the cyclodextrin derivative described above and a drug, the drug comprising at least one effective ionogenic amine, wherein at least 50 percent, by weight, of the drug present in the composition is ionically bonded to the cyclodextrin derivative. In one embodiment, the composition comprises between 1 and 30 (e.g., between 10 and 20) percent, by weight, of the drug. In a further embodiment, the drug is a polypeptide. In still a further embodiment, the polypeptide comprises between 4 and 200 amino acids (e.g., between 4 and 50 amino acids). Examples of the polypeptide include somatostatin, bombesin, calcitonin, amylin, parathyroid hormone, parathyroid hormone related protein, gastrin releasing peptide, luteinizing hormone releasing hormone, growth hormone, growth hormone releasing factor, interferons, erythropoietin, granulocyte colony stimulating factor, granulocyte macrophage colony stimulating factor, pituitary adenylate cyclase activating polypeptide, vasoactive intestinal peptide, thyrotropin releasing hormone, corticotropin releasing hormone, Acetyl-Ser-Asp-Lys-Pro, arginine vasopressin, angiotensin, and any fragments, agonists, or antagonists thereof.

In yet another aspect, the invention features a composition comprising the copolymer described above and a drug, the drug comprising at least one effective ionogenic amine, wherein at least 50 percent, by weight, of the polypeptide present in the composition is ionically bonded to the cyclodextrin derivative. In one embodiment, the composition comprises between 1 and 30 (e.g., between 10 and 20) percent, by weight, of the drug. In a further embodiment, the drug is a polypeptide.

As used herein, "lower alkyl" is intended to include both branched and straight-chain saturated aliphatic hydrocarbon groups. Examples of lower alkyl groups include methyl, ethyl, propyl, isopropyl, butyl, t-butyl, isobutyl, sec-butyl, and the like. "Lower alkenyl" groups include those branched and straight chain aliphatic hydrocarbon groups having one or several double bonds. Examples of alkenyl groups include vinyl, allyl, isopropenyl, butenyl, pentenyl, hexenyl, 1-propenyl, 2-butenyl, 2-methyl-2-butenyl, isoprenyl, and the like. All alkyl, alkenyl, and alkynyl groups are noncyclic.

As used herein, "aryl" is intended to include any stable monocyclic, bicyclic, or tricyclic carbon ring(s) of up to 7 members in each ring, wherein at least one ring is aromatic. Examples of aryl groups include phenyl, naphthyl, anthracenyl, biphenyl, tetrahydronaphthyl, indanyl, phenanthreynl, and the like. The term "carboxy" is meant to include the recited chemical group (e.g., alkyl, alkenyl, aryl, arylalkyl, arylalkenyl) substituted with 1 to 3 carboxy groups.

Other features and advantages of the present invention will be apparent from the detailed description of the invention, and from the claims.

DESCRIPTION OF THE INVENTION

It is believed that one skilled in the art can, based on the description herein, utilize the present invention to its fullest extent. The following specific embodiments are, therefore, to be construed as merely illustrative, and not limitative of the remainder of the disclosure in any way whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference.

EXAMPLE 1

Preparation of Acylated β-Cyclodextrin (ACD)

Cyclodextrin (Amaizo, American Maize Products Corp. Hammond, Ind.) was dried at 90° C. under reduced pressure (0.1 mm Hg) to a constant weight. Dried cyclodextrin (CD) was then transferred to a reaction flask equipped for stirring.

After purging with argon, the CD was heated at 50° C. for 30 min. at 0.1 mm Hg, cooled to 25° C., and repurged with dry argon. Calculated amount of the acylating reagent, as a liquid anhydride (except in ADC No. 1 where the anhydrides were dissolved in 15 ml of acetic acid), containing a catalytic amount (i.e., 1 percent by weight) of p-toluene sulfonic acid (except in ACD No. 1 and ACD No. 2 where 1 percent $H_2SO_4$ was used instead of p-toluene sulfonic acid) was transferred to the reaction flask, mixed under a dry argon atmosphere, and then heated. The amount of CD and acylating agents used as well as the heating scheme is described in Table I. At the conclusion of the reaction, the resulting mixture was allowed to cool slightly and then poured on to a vigorously stirring ice-water mixture. The resulting precipitate was filtered, rinsed several times with cold water, and air dried. The product was then isolated and dried until constant weight under vacuum, first at 25° C. and then 50° C. The product was characterized for equivalent weight, as reported in Table I, by measuring titratable carboxylic acid functionally using benzyl alcohol solution of the product and potassium hydroxide in benzyl alcohol with bromophenol red as an indicator.

TABLE I

Preparation and Properties of Acylated β-Cyclodextrins (ACD)

| ACD No. | REACTANTS[1] | HEATING SCHEME Temp (° C.)/ Time (min.) | EQUIVALENT WEIGHT (Da) |
|---|---|---|---|
| 1 | 51.0 g CD, 55.0 g A, 28.7 g S | 95/180 | 1104 |
| 2 | 25.5 g CD, 28.1 g A, 14.4 g S | 95/135 | 874 |
| 3 | 12.8 g CD, 9.69 g A, 10.8 g G | 95/120 | 561 |
| 4 | 12.8 g CD, 18.0 g P, 8.20 g G | 95/15; 100/30; and 105/30 | 829 |
| 5 | 12.7 g CD, 12.2 g P, 10.7 g G | 90/60 | 657 |
| 6 | 12.7 g CD, 10.1 g P, 13.9 g G | 70/20 | 524 |
| 7 | 12.7 g CD, 10.1 g P, 13.9 g G | 60/10 and 65/30 | 511 |
| 8 | 12.7 g CD, 12.3 g B, 13.9 g G | 60/10 and 65/45 | 574 |
| 9 | 12.7 g CD, 8.90 g B, 20.5 g G | 65/10 and 60/50 | 401 |
| 10 | 12.7 g CD, 5.31 g B, 20.4 g G | 65/5 and 60/50 | 346 |

[1]CD is β-Cyclodextrin, A is Acetic Anhydride, P is Propionic Anhydride, B is Butyric Anhydride, S is Succinic Anhydride, and G is Glutaric Anhydride

EXAMPLE 2

Grafting Acylated Cyclodextrin (G-ACD) with Lactones

Predetermined amounts of the above acylated cyclodextrin derivative (ACD), lactone or mixture of lactones, and a catalytic amount (i.e., <0.2 percent by weight) of stannous octoate were transferred to a dry polymerization flask equipped for stirring, under an inert dry atmosphere. The amount of ACD and lactones used are described in Table II. The mixture was then heated under vacuum at about 45° C. for 30 min., cooled to room temperature, and then purged with dry argon. The reactants were then heated while stirring as described in Table II. At the conclusion of the reaction, the temperature was lowered to abut 110° C., and vacuum was applied for 0.5 to 1 hr. to remove distillable volatiles. The polymerization flask was cooled to room temperature and purged with argon. The grafted copolymer product (G-ACD) was isolated, dissolved in acetone, and then precipitated in ice water. The precipitate was filtered and air dried. The resulting powder was further dried under vacuum to a constant weight. The product was characterized for equivalent weight, as reported in Table II, by measuring titratable carboxylic acid functionality.

TABLE II

Preparation of Lactone-Grafted ACD (G-ACD)

| G-ACD No. | REACTANTS[1] | HEATING SCHEME Temp (° C.)/ Time (Hr.) | EQUIVALENT WEIGHT (Da) |
|---|---|---|---|
| 1 | 2.50 ACD No. 4, 7.90 g L, 2.10 g G | 150/6 | 2060 |
| 2 | 2.50 ACD No. 3, 7.90 g L, 2.10 g G | 150/7 | 1055 |
| 3 | 4.00 ACD No. 7, 6.32 g L, 1.68 g G | 150/6.5 | 1100 |
| 4 | 2.67 ACD No. 7, 6.32 g L, 1.68 g G | 150/10.5 | 1148 |
| 5 | 3.30 ACD No. 7, 6.27 g CL, 0.34 g G | 150/10 | 1072 |
| 6 | 2.66 ACD No. 8, 6.32 g L, 1.68 g G | 150/7 | 945 |
| 7 | 5.34 ACD No. 9, 12.65 g L, 3.37 g G | 150/3.5 | 681 |

[1]G is glycolide, L is D,L-Lactide, and CL is ε-Caprolactone

EXAMPLE 3

Preparation of Polypeptide Composition Containing of Acylated β-Cyclodextrin (U-CON)

Predetermined amount of the above acylated β-cyclodextrin (ACD) was dissolved in a minimum volume of acetone (from 5–15 weight/volume percent) and filtered through a micro-syringe with 0.45 μm porous filter. The filtrate was cooled and a 1N sodium hydroxide aqueous solution was added to neutralize carboxylic groups in the ACD. A concentrated, cold solution (3–15 weight/volume percent) of the acetate salts of the polypeptides Lanreotide™ (D-Nal-c[Cys-Tyr-D-Trp-Lys-Val-Cys]-Thr-$NH_2$; Kinerton Ltd., Dublin, Ireland) or Decapeptyl™ (pGlu-His-Trp-Ser-Tyr-D-Trp-Leu-Arg-Pro-Gly-$NH_2$; Kinerton Ltd.) was added to acetone solution of the neutralized ACD dropwise with stirring. The product was left at 25° C. for 0.5–1 hr. and then precipitated in a stirring ice-water bath. The resulting precipitate was filtered, rinsed thoroughly with water, and air dried. The product was then isolated and dried under vacuum to constant weight at room temperature. The weight of the dried composition was determined, and the composition was characterized for percent content of peptide, as measured by elemental analysis of the percent of nitrogen present in the composition (Quantitative Technologies, Inc., Whitehouse, N.J.), as reported in Table III. The particulate product was reduced in size by grinding to achieve an average particle size of about 100 μ before storage under reduced pressure.

TABLE III

Preparation and Properties of Polypeptide/ Acylated β-Cyclodextrin Conjugates (U-CON)

| U-CON No. | REACTANTS[1] | PERCENT NITROGEN | PERCENT PEPTIDE |
|---|---|---|---|
| 1 | 0.00 g ACD No. 1, 0.01 g L | 0.54 | 3.84 |
| 2 | 0.10 g ACD No. 2, 0.02 g L | 1.40 | 9.96 |
| 3 | 0.035 ACD No. 4, 0.016 g L | 1.42 | 10.11 |
| 4 | 0.08 g ACD No. 3, 0.028 g L | 2.47 | 17.58 |
| 5 | 0.074 g ACD No. 5, 0.928 g L | 2.72 | 19.36 |
| 6 | 0.819 g ACD No. 5, 0.215 g L | 2.18 | 15.50 |
| 7 | 0.811 g ACD No. 5, 0.212 g L | 2.00 | 14.20 |
| 8 | 0.803 g ACD No. 4, 20.199 g L | 2.42 | 17.20 |
| 9 | 3.00 g ACD No. 5, 0.502 g L | 2.20 | 15.60 |
| 10 | 2.005 g ACD No. 4, 0.500 g D | 2.49 | 17.70 |
| 11 | 0.201 g ACD No. 7, 0.051 g D | 2.19 | 12.10 |
| 12 | 0.402 g ACD No. 6, 0.131 g D | 3.75 | 20.72 |

TABLE III-continued

Preparation and Properties of Polypeptide/
Acylated β-Cyclodextrin Conjugates (U-CON)

| U-CON No. | REACTANTS[1] | PERCENT NITROGEN | PERCENT PEPTIDE |
|---|---|---|---|
| 13 | 0.??? ACD No. 8, 0.202 g D | 3.68 | 20.33 |
| 14 | 2.004 g ACD No. 8, 0.671 g L | 1.45 | 10.32 |
| 15 | 0.601 g ACD No. 9, 0.202 g D | 3.34 | 18.45 |
| 16 | 1.2015 g ACD No. 10, 0.401 g D | 4.45 | 24.58 |
| 17 | 2.055 g ACD No. 9, 0.671 g L | 2.57 | 18.29 |

[1]L is Lanreotide™ and D is Decapeptyl™

EXAMPLE 4

Preparation of Polypeptide Conjugates of Lactone-Grafted Acylated β-Cyclodextrin (G-CON)

Predetermined amount of the grafted ACD (G-ACD) was converted to a peptide composition following the same procedure used in preparing the U-CON's in Example 3. Reaction composition and characterization data of the different G-CON's are reported in Table IV.

TABLE IV

Preparation and Properties of Polypeptide/
Lactone-Grafted ACD Conjugates (G-CON)

| G-CON No. | REACTANTS[1] | PERCENT NITROGEN | PERCENT PEPTIDE |
|---|---|---|---|
| 1 | 0.079 g G-ACD No. 1, 0.027 g L | 0.62 | 4.41 |
| 2 | 0.077 g G-ACD No. 2, 0.028 g L | 1.00 | 7.12 |
| 3 | 1.00 g G-ACD No. 3, 0.252 g L | 0.96 | 6.80 |
| 4 | 1.99 g G-ACD No. 4, 0.502 g L | 0.74 | 5.30 |
| 6 | 0.202 g G-ACD No. 4, 0.051 g D | 0.53 | 2.92 |
| 7 | 2.003 g G-ACD No. 5, 0.5019 g L | 1.16 | 8.26 |
| 8 | 1.206 g G-ACD No. 6, 0.4015 g D | 1.98 | 10.93 |
| 9 | 1.2035 g G-ACD No. 7, 0.4036 g D | 3.56 | 19.67 |
| 10 | 2.0078 g G-ACD No. 6, 0.6706 g L | 1.69 | 12.03 |

[1]L is Lanreotide ™ and D is Decapeptyl ™

EXAMPLE 5

In Vivo Release Assay

Male Sprague-Dawley rats (200–225 g; Taconic Farms) were injected intermuscularly with approximately 3 ml of either 767 mg of G-CON-19 or 922 mg of U-CON-16 or 966 mg of U-CON-16 administered in a vehicle of 2% carboxymethyl cellulose/1% Tween 20/saline. Blood samples were taken by 6 hours, 2 days, 7 days, 15 days and 22 days following administration. The concentration of Lanreotide™ in the blood was measured by standard radioimmunoassay and is reported in the following Table V.

TABLE V

Lanreotide ™ Release in Rat Plasma

| COMPOSITION | PLASMA LANREOTIDE (pg/ml) | | | | |
|---|---|---|---|---|---|
| | 6 HRS. | DAY 2 | DAY 7 | DAY 15 | DAY 22 |
| U-CON-19 | 67006 | 33921 | 19690 | 6115 | 1691 |
| U-CON-16 | 61338 | 24347 | 7649 | 1621 | 766 |

Thus, both the ungrafted composition U-CON-19 and the grafted composition U-CON-16 released the drug Lanreotide™ over a period of at least 22 days.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A composition comprising a cyclodextrin derivative and a drug, said drug comprising at least one ionogenic amine, wherein at least 60 percent of the free hydroxy groups of said cyclodextrin are acylated with acyl groups where at least one of said acyl groups comprises a free carboxylic group, wherein at least 50 percent, by weight, of said drug present in said composition is ionically bonded to said cyclodextrin derivative.

2. The composition of claim 1, wherein said composition comprises between 1 and 30 percent, by weight, of said drug.

3. The composition of claim 2, wherein said drug is a polypeptide.

4. The composition of claim 3, wherein said polypeptide comprises between 4 and 50 amino acids.

5. The composition of claim 4, wherein said polypeptide is somatostatin, LHRH, calcitonin, or an analog thereof.

6. A composition of claim 5, wherein said LHRH analog is pGlu-His-Trp-Ser-Tyr-D-Trp-Leu-Arg-Pro-Gly-NH$_2$.

7. The composition of claim 5, wherein said somatostatin analog is D-Nal-c[Cys-Tyr-D-Trp-Lys-Val-Cys]-Thr-NH$_2$.

8. A composition comprising a copolymer and a drug, said drug comprising a polypeptide having at least one ionogenic amine, said copolymer comprising a cyclodextrin derivative, wherein at least 60 percent of the free hydroxy groups of said cyclodextrin derivative are acylated with acyl groups, where at least one of said acyl groups comprises a free carboxylic group, and said cyclodextrin derivative further comprises at least one free hydroxy group which is acylated with a polyester comprising hydroxy acid monomers, and wherein at least 50 percent, by weight, of said polypeptide present in said composition is ionically bonded to said cyclodextrin derivative.

9. The composition of claim 8, wherein said composition comprises between 1 and 30 percent, by weight, of said drug.

10. The composition of claim 9, wherein said drug is a polypeptide.

11. The composition of claim 10, wherein said polypeptide comprises between 4 and 50 amino acids.

12. The composition of claim 11, wherein said polypeptide is somatostatin, LHRH, calcitonin, or an analog thereof.

13. A composition of claim 12, wherein said LHRH analog is pGlu-His-Trp-Ser-Tyr-D-Trp-Leu-Arg-Pro-Gly-NH$_2$.

14. A composition of claim 12, wherein said somatostatin analog is D-Nal-c[Cys-Tyr-D-Trp-Lys-Val-Cys]-Thr-NH$_2$.

* * * * *

UNITED STATES PATENT AND TRADEMARK OFFICE
CERTIFICATE OF CORRECTION

PATENT NO. : 6,204,256 B1
DATED : March 20, 2001
INVENTOR(S) : Shalaby Wahba Shalaby and Joel Thomas Corbett It is certified that error appears in the above-identified patent and that said Letters Patent is hereby corrected as shown below:

<u>Title page,</u>
Item [73], Assignee: Polymed. Fendleton. SC (US) delete "Fendleton" and insert
-- Pendleton --

Signed and Sealed this

Nineteenth Day of February, 2002

Attest:

JAMES E. ROGAN
*Director of the United States Patent and Trademark Office*

*Attesting Officer*